(12) United States Patent
Brough et al.

(10) Patent No.: US 6,649,373 B2
(45) Date of Patent: Nov. 18, 2003

(54) USE OF TRANS-ACTIVATION AND CIS-ACTIVATION TO MODULATE THE PERSISTENCE OF EXPRESSION OF A TRANSGENE

(75) Inventors: Douglas E. Brough, Olney, MD (US); Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 18 days.

(21) Appl. No.: 09/873,486

(22) Filed: Jun. 4, 2001

(65) Prior Publication Data

US 2002/0031823 A1 Mar. 14, 2002

Related U.S. Application Data

(63) Continuation of application No. PCT/US99/28637, filed on Dec. 3, 1999, which is a continuation-in-part of application No. 09/205,014, filed on Dec. 4, 1998, now Pat. No. 6,225,113.

(51) Int. Cl.$^7$ .................. C12N 15/09; C12N 15/86; C12N 15/85; C12N 5/10
(52) U.S. Cl. .................. 435/69.1; 435/91.1; 435/455; 435/465; 435/320.1; 435/235.1; 435/325
(58) Field of Search ............... 435/69.1, 91.1, 435/455, 465, 320.1, 235.1, 325

(56) References Cited

U.S. PATENT DOCUMENTS

| | | | |
|---|---|---|---|
| 4,518,584 A | 5/1985 | Mark et al. |
| 4,737,462 A | 4/1988 | Mark et al. |
| 6,040,174 A | 3/2000 | Imler et al. |

FOREIGN PATENT DOCUMENTS

| | | |
|---|---|---|
| WO | WO 95/26412 A | 10/1995 |
| WO | WO 95/31566 A | 11/1995 |
| WO | WO 97/46687 A | 12/1997 |

OTHER PUBLICATIONS

Block et al, Journal of General Virology 72:131–141, 1991.*
Zhu et al (Journal of Virology 62:4544–4553, 1988).*
Samaniego et al (Journal of Virology 72:3307–3320, Apr. 1998).*
Nordqvist et al., *Mol. Biol. Rep., 14*, 203–204 (1990).
Agarwal et al., *J. Virol., 72* (5), 3720–3728 (May 1998).
Ahn et al., *Mol. Cell. Biol., 18* (8), 4899–4913 (Aug. 1998).
Armentano et al., *J. Virol., 71* (3), 2408–2416 (Mar. 1997).
Bauer et al., *Gene, 37* (1–3), 73–81 (1985).
Berkner, *BioTechniques, 6* (7), 616–629 (Jul./Aug. 1988).
Bresnahan et al., *J. Biol. Chem., 272* (34), 22075–22082 (Aug. 21, 1998).
Brough et al., *J. Virol., 70* (9), 6497–6501 (Sep. 1996).
Brough et al., *J. Virol., 71* (12), 9206–9213 (Dec. 1997).
Cotten et al., *PNAS USA, 89* (13), 6094–6098 (Jul. 1, 1992).
Craik, *BioTechniques, 3* (1), 12–19 (Jan. 1985).
Crystal, *Science, 270* (5235), 404–410 (Oct. 20, 1995).
Curiel et al., *Hum. Gene Ther., 3* (2), 147–154 (Apr. 1992).
Curiel et al., *PNAS USA, 88* (19), 8850–8854 (Oct. 1, 1991).
Dai et al., *PNAS USA, 92* (5), 1401–1405 (Feb. 25, 1995).
Devereux et al., *Nucleic Acids Res., 12* (1, pt. 1), 387–395 (Jan. 11, 1984).
Di Pasquale et al., *J. Virol., 72* (10), 7916–7925 (Oct. 1998).
Dobner et al., *Science, 272* (5267), 1470–1473 (Jun. 7, 1996).
Gebert et al., *J. Virol., 71* (9), 7048–7060 (Sep. 1997).
Goodrum et al., *J. Virol., 70* (9), 6323–6335 (Sep. 1996).
Guerette et al., *Transplantation, 62* (7), 962–967 (Oct. 15, 1996).
Henkart, *Immunity, 1* (5), 343–346 (Aug. 1994).
Jaffe et al., *Clin. Res., 39* (2), 302A (1991).
Javier et al., *Breast Cancer Res. Treat., 39* (1), 57–67 (1996).
Javier et al., *J. Virol., 65* (6), 3192–3202 (Jun. 1991).
Javier et al., *J. Virol., 68* (6), 3917–3924 (Jun. 1994).
Javier et al., *Science, 257* (5074), 1267–1271 (Aug. 28, 1992).
Jenuwein et al., *Nature, 385* (6613), 269–272 (Jan. 16, 1997).
Jordan et al., *J. Virol., 71* (9), 6850–6862 (Sep. 1997).
Jordan et al., *J. Virol., 72* (7), 5373–5382 (Jul. 1998).
Kägi et al., *Eur. J. Immunol., 25* (12), 3256–3262 (Dec. 1995).
Kägi et al., *Science, 265* (5171), 528–530 (Jul. 22, 1994).
Kalos et al., *Mol. Cell. Biol., 15* (1), 198–207 (Jan. 1995).
Kass–Eisler et al., *Gene Therapy, 1* (6), 395–402 (Nov. 1994).
Kay et al., *Nat. Genet., 11* (2), 191–197 (Oct. 1995).
Kojima et al., *Immunity, 1* (5), 357–364 (Aug. 1994).
Kolls et al., *Hum. Gene Ther., 7* (4), 489–497 (Mar. 1, 1996).
Li et al., *Hum. Gene Ther., 4* (4), 403–409 (Aug. 1993).
Lieber et al., *Nature/Biotech., 15* (13), 1383–1387 (Dec. 1997).
Luckow et al., *Bio/Technology, 6*, 47–55 (Jan. 1988).
Marcellus et al., *J. Virol., 70* (9), 6207–6215 (Sep. 1996).
Moriuchi et al., *Virology, 209* (1), 281–283 (May 10, 1995).
Müller et al., *J. Virol., 66* (10), 5867–5878 (Oct. 1992).

(List continued on next page.)

*Primary Examiner*—Mary E. Mosher
(74) *Attorney, Agent, or Firm*—Leydig, Voit & Mayer, Ltd.

(57) ABSTRACT

Provided are methods of modulating the persistence of the expression in a cell of a transgene, such as a transgene in a non-Herpes vector or in at least E4Δ adenoviral vector, and related systems. One method comprises contacting the cell with a non-Herpes vector comprising and expressing a gene encoding HSV ICP0, whereupon expression of HSV ICP0 the persistence of expression of the transgene is modulated. Further provided is a system for modulating the persistence of expression of a transgene, which system comprises a non-Herpes vector comprising (i) a gene encoding HSV ICP0 and (ii) a transgene, wherein the HSV ICP0 modulates the persistence of expression of the transgene and either the non-Herpes vector comprises the transgene or the system further comprises a vector, in which case the vector comprises the transgene.

6 Claims, No Drawings

OTHER PUBLICATIONS

Nevels et al., *PNAS USA*, 94 (4), 1206–1211 (Feb. 18, 1997).
Nevins, *Virus Res.*, 20 (1), 1–10 (Jun. 1991).
Nordqvist et al., *Mol. Cell. Biol.*, 14 (1), 437–445 (Jan. 1994).
Öhman et al., *Virology*, 194 (1), 50–58 (May 1993).
Pereira et al., *J. Virol.*, 71 (2), 1079–1088 (Feb. 1997).
Rosenfeld et al., *Clin. Res.*, 39 (2), 311A (1991).
Rosenfeld et al., *Science*, 252 (5004), 431–434 (Apr. 19, 1991).
Rossi et al., *Curr. Opin. Biotechnol.*, 9 (5), 451–456 (Oct. 1998).
Samaniego et al., *J. Virol.*, 72 (4), 3307–3320 (Apr. 1998).
Sandler et al., *J. Virol.*, 63 (2), 624–630 (Feb. 1989).
Sandler et al., *Virology*, 181 (1), 319–326 (Mar. 1991).
Sarisky et al., *J. Virol.*, 70 (11), 7393–7413 (Nov. 1996).
Schafer et al., *J. Virol.*, 70 (10), 6937–6946 (Oct. 1996).
Tan et al., *J. Virol.*, 72 (5), 3610–3622 (May 1998).
Wagner et al., *PNAS USA*, 89 (13), 6099–6103 (Jul. 1, 1992).
Walder et al., *Gene*, 42 (2), 133–139 (1986).
Watkins et al., *Immunotechnology*, 2 (4), 307 (1996).
Weiss et al., *J. Virol.*, 70 (2), 862–872 (Feb. 1996)
Weiss et al., *J. Virol.*, 71 (3), 1857–1870 (Mar. 1997).
Weiss et al., *J. Virol.*, 71 (6), 4385–4393 (Jun. 1997).
Worgall et al., *Hum. Gene Ther.*, 8 (1), 37–44 (Jan. 1, 1997).
Yang et al., *J. Immunol.*, 155 (5), 2564–2570 (Sep. 1, 1995).
Yang et al., *PNAS USA*, 91 (10), 4407–4411 (May 10, 1994).
Yang et al., *PNAS USA*, 92 (16), 7257–7261 (Aug. 1, 1995).
Yao et al., *J. Virol.*, 69 (10), 6249–6258 (Oct. 1995).
Zhu et al., *J. Virol.*, 62 (12), 4544–4553 (Dec. 1988).
Watanabe et al., *J. Gen. Virol.*, 76 (Part 11), 2881–2885 (Nov. 1995).
Weger et al., *J. Virol.*, 71 (11), 8437–8447 (Nov. 1997).

\* cited by examiner

USE OF TRANS-ACTIVATION AND CIS-ACTIVATION TO MODULATE THE PERSISTENCE OF EXPRESSION OF A TRANSGENE

This application is a continuation of International Patent Application No. PCT/US99/28637, filed Dec. 3, 1999, which is a continuation-in-part of U.S. patent application Ser. No. 09/205,014, filed Dec. 4, 1998, now U.S. Pat. No. 6,225,113.

TECHNICAL FIELD OF THE INVENTION

This invention relates to cis- and trans-activation methods of modulating the persistence of expression of a transgene in non-Herpes vectors, more particularly in at least E4-deficient (E4Δ) adenoviral vectors, as well as transactivation systems for use in such methods.

BACKGROUND OF THE INVENTION

Gene therapy relies upon the introduction of one or more recombinant nucleic acid molecules (i.e., vectors) comprising one or more transgenes into a host (e.g., a human), wherein the presence, and in most cases the expression, of the transgene produces some desired effect (e.g., production of a therapeutic protein). Thus, for gene therapy to be effective, vectors (particularly, gene transfer vectors) that provide persistent expression of the transgene are desired.

Using vector reporter gene constructs, it has been established that high levels of vector transgene expression can be obtained in a variety of animal models. However, it also has been established that the high level of transgene expression so obtained is transient, with reporter gene expression peaking within the first week after infection and becoming essentially undetectable about 80 days after infection. Recent studies have indicated that the limited persistence of gene expression in vivo is most likely due to an immune response of the host against virally infected cells. For example, gene expression can be maintained in immunologically privileged neuronal or retinal tissues for periods in excess of two months and in immunodeficient or immunologically naïve rodents for periods in excess of six months. Transgene expression in immune-competent animals, by contrast, rapidly declines to baseline levels within 2–3 weeks of infection due to immune activation.

Using a combination of mouse strains, which are defective in specific elements of the immune system, it has been shown that the immune response against cells infected with viral vectors involves both cellular and humoral components of the immune system. For example, immunodeficient mice, which lack mature T- and B-lymphocytes, express adenovirus-mediated transgenes beyond four months (Kass-Eisler et al., Gene Therapy 1: 395–402 (1994); Yang et al., Immunity 1: 433–442 (1994a); Yang et al., PNAS USA 91: 4407–4411 (1994b); Dai et al., PNAS USA 92: 1401–1405 (1995); Kay et al., Nat. Genet. 11: 191–197 (1995); and Yang et al., J. Immunol. 155: 2564–2570 (1995)). Similarly, transfer of CD8$^+$ and CD4$^+$ cytotoxic T-cells from adenoviral vector-infected mice to infected RAG-2 mice, which lack mature B- and T-lymphocytes, results in clearance of the vector and the transgene by apoptosis (Yang et al. (1994a), supra; and Yang et al. (1995), supra), whereas immune depletion of CD8$^+$ or CD4$^+$ cells in immunocompetent mice results in persistent transgene expression (Yang et al. (1994a), supra; Kay et al., Nat. Genet. 11: 191–197 (1995); Yang et al. (1995), supra; Kolls et al., Hum. Gene Ther. 7: 489–497 (1996); and Guerette et al., Transplantation 62: 962–967 (1996)). While pathways involving perforin and Fas are the major pathways responsible for T-cell cytotoxicity (Kojima et al., Immunity 1: 357–364 (1994); Henkart, Immunity 1: 343–346 (1994); Kagi et al., Science 265: 528–530 (1994); and Kagi et al., Eur. J. Immunol. 25: 3256–3262 (1995)), the perforin/granzyme pathway has been reported to mediate clearance of adenoviral gene transfer vectors by antigen-specific, cytotoxic T-cells (Yang et al., PNAS USA 92: 7257–7261 (1995)).

In addition to limiting the persistence of gene expression from viral vectors, the immune response inhibits successful readministration of viral vectors, which limits the period of gene expression. For example, adenoviruses are classified into 47 different serotypes and a number of subgroups, namely A through G, based on a number of criteria, including antigenic cross-reactivity. Following an initial administration of adenovirus, serotype-specific antibodies are generated against epitopes of the major viral capsid proteins, namely the penton, hexon and fiber. Given that such capsid proteins are the means by which the adenovirus attaches itself to a cell and subsequently infects the cell, such antibodies (i.e., neutralizing antibodies) are then able to block or "neutralize" reinfection of a cell by the same serotype of adenovirus. This necessitates using a different serotype of adenovirus in order to administer one or more subsequent doses of exogenous DNA to continue to express a given gene, such as in the context of gene therapy.

Another approach to increasing the persistence of transgene expression in vector systems involves the introduction of substantial deletions in a viral vector so as to reduce or eliminate completely the production of viral antigens by the viral vector. In this regard, the deletion of E4 from adenoviral vectors is especially important for safe adenoviral vector design. Removal of the E4 region severely disrupts adenoviral gene expression in transduced cells. Removal of the E4 region also eliminates several viral products that interact with and antagonize cellular targets and processes. E4-ORF6 has been shown to block p53 function and to have oncogenic potential (Dobner et al., Science 272: 1470–1473 (1996); Nevels et al., PNAS USA 94: 1206–1211 (1997)). It also appears that E4-ORF1 has oncogenic potential (Javier et al., J. Virol. 65: 3192–3202 (1991); Javier et al., Science 257: 1267–1271 (1992); Javier et al., Breast Cancer Res. Treat. 39: 57–67 (1996); Javier et al., J. Virol. 68: 3917–3924 (1994); Weiss et al., J. Virol. 71: 4385–4393 (1997); Weiss et al., J. Virol. 71: 1857–1870 (1997); and Weiss et al., J. Virol. 70: 862–872 (1996)). ORF6 and ORF3 of the E4 region of adenovirus also have been shown to be involved in altering mRNA expression post-transcriptionally (Nordqvist et al., PNAS USA 87: 9543–9547 (1990); Nordqvist et al., Mol. Cell. Biol. 14: 437–445 (1994); Nordqvist et al., Mol. Biol. Rep. 14: 203–204 (1990); Ohman et al., Virology 194: 50–58 (1993); Sandler et al., J. Virol. 63: 624–630 (1989); and Sandler et al., Virology 181: 319–326 (1991)). E4 products are also involved in controlling E2F (Nevins, Virus Res. 20: 1–10 (1991)), E1A-induced p53-independent apoptosis (Marcellus et al., J. Virol. 70: 6207–6215 (1996)), the modulation of the phosphorylation status of cellular and viral proteins (Kleinberger et al. 67: 7556–7560 (1993); and Muller et al., J. Virol. 66: 5867–5878 (1992)), and the alteration of the nuclear transport of various proteins (Goodrum et al., J. Virol. 70: 6323–6335 (1996)). Elimination of the E4 region of adenovirus eliminates these negative effects. However, E4 elimination also adversely affects maintenance of transgene persistence.

Provision of E4 in trans has been proposed as a method of activating transgene expression from an E4Δ adenoviral vector (Brough et al., J. Virol. 71(12): 9206–9213 (1997)). Supply of E4 products in trans has been demonstrated to allow persistent expression from the cytomegalovirus E4 promoter (Armentano et al., J. Virol. 71(3): 2408–2416 (1997)). One potential problem associated with any administration of E4 products is that a multiplicity of E4 containing vectors has been found to result in cell toxicity, particularly in endothelial cells. Co-expression of the adenoviral E2 preterminal protein from an adenoviral vector or in trans has been demonstrated to stabilize in vitro an adenoviral minigenome, which is deficient in E1, E2 and E3 but not E4 (Lieber et al., Nature Biotech. 15: 1383–1387 (1997)). Expression of a transgene operably linked to the cytomegalovirus (CMV) immediate early promoter has been demonstrated to be dependent on the infected cell protein 0 in *Herpes simplex* vectors; based on such a showing, it was suggested that ORF3 of the E4 region of adenovirus could have the same effect on transgene expression in an adenoviral vector (Samaniego et al., J. Virol. 72(4): 3307–3320 (1998)).

Adenoviruses in many settings are advantageous as viral vectors because they are easy to use, can be produced in high titers (i.e., up to about $10^{13}$ viral particles/ml), transfer genes efficiently to nonreplicating, as well as replicating, cells (see, for example, review by Crystal, Science 270: 404–410 (1995)), and exhibit a broad range of host- and cell-type specificity. Such advantages have resulted in a recombinant adenovirus being the vector of choice for a variety of gene transfer applications. Adenoviral vectors are especially preferred for somatic gene therapy of the lungs, given their normal tropism for the respiratory epithelium.

Other advantages that accompany the use of adenoviruses as vectors in in vivo gene expression include: (1) the rare observance of recombination; (2) the absence of an ostensible correlation of any human malignancy with adenoviral infection, despite the common occurrence of infection; (3) the adenoviral genome (which is comprised of linear, double-stranded DNA) can be manipulated to carry up to about 7.5 kb of exogenous DNA, and longer DNA sequences can potentially be carried into a cell, for instance, by attachment to the adenoviral capsid (Curiel et al., Human Gene Therapy 3: 147–154 (1992)); (4) an adenovirus can be modified such that it does not interfere with normal cellular function, given that the vector controls expression of its encoded sequences in an epichromosomal manner; and (5) it already has been proven safe to use in humans, given that live adenovirus has been safely used as a human vaccine for many years.

Intravenous administration of adenovirus to mice results in the vast majority of adenovirus being localized to the liver (Worgall et al., Human Gene Therapy 8: 37–44 (1997)). During the first 24–48 hrs of infection, 90% of vector DNA is eliminated, presumably through innate pathways of viral clearance mediated by Kupffer cells in the liver (Worgall et al. (1997), supra), well before maximal levels of transgene are expressed. In spite of the fact that the majority of virus is cleared within one to two days, over 95% of hepatocytes are transduced by the remaining small percentage of input adenoviral vectors (Li et al., Human Gene Therapy 4: 403–409 (1993)) with maximum transgene expression occurring during the first week of post-infection.

In view of the above, there is a need in the art for other methods and compositions than those known in the art that effect persistent transgene expression in vector systems. More particularly, there is a need for such methods and compositions for vectors that are useful in gene therapy, such as adenoviral gene transfer vectors.

The present invention seeks to address some of the disadvantages inherent to the methods and vectors of the prior art by providing, among other things, methods and vectors or systems that modulate the persistence of expression of a transgene in a cell. This and other objects and advantages of the present invention, as well as additional inventive features, will be apparent from the following detailed description.

BRIEF SUMMARY OF THE INVENTION

The present invention provides methods of modulating the persistence of the expression in a cell of a transgene, such as a transgene in a non-Herpes vector or in at least E4Δ adenoviral vector. One method comprises contacting the cell with a non-Herpes vector comprising and expressing a gene encoding HSV ICP0, whereupon expression of HSV ICP0 the persistence of expression of the transgene is modulated. In this regard, the present invention further provides a system for modulating the persistence of expression of a transgene, which system comprises a non-Herpes vector comprising (i) a gene encoding HSV ICP0 and (ii) a transgene, wherein the HSV ICP0 modulates the persistence of expression of the transgene and either the non-Herpes vector comprises the transgene or the system further comprises a vector, in which case the vector comprises the transgene.

Another method comprises contacting the cell with an at least E4Δ adenoviral vector comprising (i) a transgene and (ii) a gene encoding a trans-acting factor, which is not from the E4 region of an adenovirus and which modulates the persistence of expression of the transgene. In another embodiment of this method, i.e., a two vector embodiment, the method comprises contacting the cell simultaneously or sequentially with (i) an at least E4Δ adenoviral vector comprising a transgene and (ii) a viral vector comprising a gene encoding a trans-acting factor, which is not from the E4 region of an adenovirus and which modulates the persistence of expression of the transgene. In this regard, the present invention further provides a system for modulating the persistence of expression of a transgene in an at least E4Δ adenoviral vector, which system comprises (i) an at least E4Δ adenoviral vector comprising a transgene and (ii) a viral vector comprising a gene encoding a trans-acting factor. The gene encoding the trans-acting factor is not from the E4 region of an adenovirus and either the at least E4Δ adenoviral vector comprises the gene encoding the trans-acting factor or the system further comprises a viral vector, in which case the viral vector comprises the gene encoding the trans-acting factor. The trans-acting factor modulates the persistence of expression of the transgene.

DETAILED DESCRIPTION OF THE INVENTION

The present invention is predicated, at least in part, on the observation that an at least E4Δ adenoviral vector expresses a transgene at high levels for a limited amount of time in vivo. The present invention is further predicated on the discovery that persistence of expression of a transgene in an at least E4Δ adenoviral vector can be modulated through the action of a trans-acting factor, such as HSV ICP0 or Ad pTP, among others. The present invention is additionally based upon the discovery that persistence of expression of a transgene in a cell can be modulated by contacting the cell with any suitable non-Herpes vector, including an adenoviral gene transfer vector, that comprises and expresses a gene encoding HSV ICP0.

Accordingly, the present invention provides a method of modulating the persistence of expression of a transgene in a cell. By "transgene" is meant any gene that can be expressed in a cell. Desirably, the expression of the transgene is beneficial, e.g., prophylactically or therapeutically beneficial, to the cell or a tissue, organ, organ system, organism or cell culture of which the cell is a part. If the transgene confers a prophylactic or therapeutic benefit to the cell, the transgene can exert its effect at the level of RNA or protein. For example, the transgene can encode a protein that can be employed in the treatment of an inherited disease, e.g., the cystic fibrosis transmembrane conductance regulator can be employed in the treatment of cystic fibrosis. Alternatively, the transgene can encode an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation. The transgene can be part of an expression cassette. In the context of the present invention, if the transgene is located in the non-Herpes vector, the transgene can be located anywhere in the non-Herpes vector. Preferably, in those embodiments of the present invention when the non-Herpes vector is an adenoviral vector (such as an adenoviral gene transfer vector), the transgene is located in the E1 region of the adenoviral vector.

Any suitable non-Herpes vector can be utilized in the context of the present invention. A "non-Herpes" vector is any vector that is not substantially derived from Herpes simplex virus (HSV) and/or does not contain a substantial proportion of the Herpes simplex genome. Preferably, the non-Herpes vector of the present invention comprises three genes or less derived from HSV, more preferably two or less, and optimally only HSV ICP0 or a portion thereof responsible for trans-activation in the context of the present invention. Suitable examples of non-Herpes vectors include plasmids, cosmids, and viral vectors. Desirably, the non-Herpes vector is a viral vector, more preferably a DNA viral vector, and even more preferably a DNA viral vector that does not integrate into the host genome. More preferably still, the non Herpes vector is an adenoviral vector, more particularly an adenoviral gene transfer vector, such as an at least E4Δ adenoviral vector.

In one aspect, the present invention provides a method of modulating the persistence of expression of a transgene in a cell by contacting the cell with a non-Herpes vector comprising and expressing a gene encoding HSV ICP0, whereupon expression of HSV ICP0 the persistence of expression of the transgene is modulated. HSV ICP0 indicates the infected cell polypeptide of *Herpes simplex* virus, and thus the present invention includes use of the HSV ICP0 gene or an RNA or cDNA corresponding to the HSV ICP0 gene. The method can further comprise contacting the cell with a vector comprising a transgene. The non-Herpes vector can further comprise a cis-acting factor as described herein. Ad pTP can be used in a similar manner as HSV ICP0.

HSV ICP0 is comprised of multiple domains, encoded by different portions of the HSV ICP0 gene. It is believed that one or more of these domains may be sufficient to induce the effect(s) that are responsible for the modulation of transgenes in non-Herpes vectors. The identification of such domains can be accomplished using standard techniques known in the art. For example, by performing mutational analysis on the HSV ICP0 gene encoding the different domains (or performing similar analysis on the gene products of such domains), domains and/or regions within the domains that are responsible for such effects can be identified. An example of similar analysis using such techniques is described in Vos et al., *Virology*, 172(2): 634–42 (1989). By performing such techniques domain(s) of HSV ICP0 can be identified that can be used as trans-acting factors in modulating the persistence of transgene expression. In a similar vein, genes that demonstrate a high level of sequence homology to HSV ICP0 can be later identified from other organisms, or synthetically produced, and used as trans-acting factors in modulating the persistence of transgene expression. The identification of such genes can lead to the identification of cellular functions involved in transgene persistence. The presence of HSV ICP0 in non-Herpes vectors leads to lower production of neutralizing antibodies by a host against a non-Herpes vector, such as an adenoviral vector. The present invention, thus, has applicability in the administration of immunogenic naked DNAs.

The present invention further provides a system for modulating the persistence of expression of a transgene. The system comprises a non-Herpes vector comprising (i) a gene encoding HSV ICP0 and (ii) a transgene, wherein, the HSV ICP0 modulates the persistence of expression of the transgene and either the non-Herpes vector comprises the transgene or the system further comprises a vector, in which case the vector comprises the transgene. Such a system also can further comprise a cis-acting factor, as described elsewhere herein, either present on the non-Herpes vector and/or on the vector. Such a system can include a carrier for the system, preferably a pharmaceutically acceptable carrier, examples of which are widely known in the art and are exemplified herein.

In another aspect, the present invention provides a method for modulating the persistence and expression of a transgene in at least E4Δ adenoviral vector in a cell. By "an least E4Δ adenoviral vector" is meant an adenoviral vector that is at least deficient in the E4 region of the adenoviral genome. The vector can also be deficient in one or more other regions of the adenoviral genome, such as early regions and/or late regions. By "deficient" is meant an absence of a gene function in a given region of the adenoviral genome. In other words, the region does not comprise, encode and/or express a wild-type adenoviral gene function. In the case of the E4 region, this includes functions required for viral DNA replication, mRNA splicing and accumulation, late protein expression and inhibition of host cell protein synthesis. In the E4 region, the deficiency is desirably complete. Any deficiency in one or more other regions of the adenoviral genome can be complete or partial. The absence of gene function can be due to a deletion, an insertion or a mutation, for example. The one or more deficiencies in the adenoviral vector should be such that a transgene or an expression cassette comprising a transgene can be inserted into the adenoviral vector and expressed.

In one embodiment of the method, i.e., a single vector embodiment, the method comprises contacting the cell with an at least E4Δ adenoviral vector comprising (i) a transgene and (ii) a gene encoding a trans-acting factor. In another embodiment, i.e., a two vector embodiment, the method comprises contacting the cell simultaneously or sequentially with (i) an at least E4Δ adenoviral vector comprising a transgene and (ii) a viral vector comprising a gene encoding a trans-acting factor. In both embodiments of the method, the trans-acting factor modulates the persistence of expression of the transgene and the gene encoding the trans-activating factor is not from the E4 region of an adenovirus.

"Contacting" can be done by any means known to those skilled in the art, and described herein, by which the apparent touching or mutual tangency of the vector(s) with the cell can be effected. Optionally, the vector can be further complexed with a bi-specific or multi-specific molecule (e.g., an antibody or fragment thereof), in which case "contacting" involves the apparent touching or mutual tangency of the complex of the vector and the bi-specific or multi-specific molecule with the cell. For example, the vector and the bi-specific (multi-specific) molecule can be covalently joined, e.g., by chemical means known to those skilled in the art, or other means. Preferably, the vector and the bi-specific (multi-specific) molecule can be linked by means of noncovalent interactions (e.g., ionic bonds, hydrogen bonds, Van der Waals forces, and/or nonpolar interactions). Although the vector and the bi-specific (multi-specific) molecule can be brought into contact by mixing in a small volume of the same solution, the cell and the complex need not necessarily be brought into contact in a small volume, as, for instance, in cases where the complex is administered to a host (e.g., a human), and the complex travels by the bloodstream to the cell to which it binds selectively and into which it enters. The contacting of the vector with a bi-specific (multi-specific) molecule preferably is done before the cell is contacted with the complex of the adenovirus and the bi-specific (multi-specific) molecule.

With respect to the two vector embodiment, "simultaneously" means that the at least E4Δ adenoviral vector and the viral vector are brought into contact with a cell at the same time (or sufficiently close in time as to be considered at the same time). "Sequentially" means that the at least E4Δ adenoviral vector and the viral vector are brought into contact with a cell one after the other. If the two vectors are sequentially administered, preferably the viral vector is administered subsequently to the at least E4Δ adenoviral vector comprising the transgene. Sequential administration of the second vector, such as the viral vector, can be immediate or delayed and by the same route or a different route, e.g., intravenous or intramuscular. If sequential administration of the second vector is delayed, the delay can be a matter of minutes, hours, days, weeks, months or even longer. In this regard, sequential administration of the second vector can be delayed through the use of a time-release composition. The two vector embodiment of the method, therefore, allows for modulation in situations where there is substantial delay between the administration of the at least E4Δ adenoviral vector comprising the transgene and the viral vector comprising the gene encoding the trans-acting factor such that expression of the transgene has substantially decreased over time.

A cell can be any cell and can be present as a single entity, or can be part of a larger collection of cells. Such a larger collection of cells can comprise, for instance, a cell culture (either mixed or pure), a tissue (e.g., epithelial or other tissue), an organ (e.g., heart, lung, liver, gallbladder, urinary bladder, eye or other organ), an organ system (e.g., circulatory system, respiratory system, gastrointestinal system, urinary system, nervous system, integumentary system or other organ system), or an organism (e.g., a bird, mammal, particularly a human, or the like). Preferably, the organs/ tissues/cells are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin). Even more preferably, the cells are selected from the group consisting of heart, blood vessel, lung, liver, gallbladder, urinary bladder, and eye cells.

If a vector in accordance with the present invention is targeted to a cell (e.g., in a manner described above with respect to "contacting"), the cell to which the vector is targeted differs from another cell, which is not targeted, in that the cell so being targeted comprises a particular cell-surface binding site (e.g., that is recognized by the bi-specific (multi-specific) molecule). By "particular cell-surface binding site" is meant any site (i.e., molecule or combination of molecules) present on the surface of a cell with which the vector, e.g., adenoviral vector, can interact in order to attach to the cell and, thereby, enter the cell. A particular cell-surface binding site, therefore, encompasses a cell-surface receptor and, preferably, is a protein (including a modified protein), a carbohydrate, a glycoprotein, a proteoglycan, a lipid, a mucin molecule or mucoprotein, or the like. Examples of potential cell-surface binding sites include, but are not limited to: heparin and chondroitin sulfate moieties found on glycosaminoglycans; sialic acid moieties found on mucins, glycoproteins, and gangliosides; major histocompatability complex I (MHC I) glycoproteins; common carbohydrate molecules found in membrane glycoproteins, including mannose, N-acetyl-galactosamine, N-acetyl-glucosamine, fucose, and galactose; glycoproteins, such as ICAM-1, VCAM, E-selectin, P-selectin, L-selectin, and integrin molecules; and tumor-specific antigens present on cancerous cells, such as, for instance, MUC-1 tumor-specific epitopes. However, targeting an adenovirus to a cell is not limited to any specific mechanism of cellular interaction (i.e., interaction with a given cell-surface binding site).

Trans-acting factors are known in the art. Some trans-acting factors are secreted by cells that express them; others are not. The trans-acting factor modulates the persistence of expression of the transgene. In the context of the present invention, it is desired that the trans-acting factor not be secreted by the cell that expresses it, in which case, the trans-acting factor (and any cis-acting factor) must be expressed in the same cell as the transgene. The gene encoding the trans-acting factor is not from the E4 region of an adenovirus. A preferred trans-acting factor that is not from the E4 region of an adenovirus is Ad pTP. Preferably, the gene encoding the trans-acting factor is not from an adenovirus. The trans-acting factor can be of viral or cellular origin and can be under the control of a regulatable promoter, such as an inducible promoter (e.g., tet) or a repressible promoter, a regulatable expression system (e.g., tetracycline, rampamycin or radiation-inducible), or a cell- or tissue-type expression system as are known in the art (Rossi et al., Current Opinion in Biotechnology 9:451–456 (1998)). Examples of trans-acting factors that are not from an adenovirus include HSV ICP0 (Jordan et al., J. Virol. 71:6850–6862 (1997); and Moriuchi et al., Virology 209: 281–283 (1995)), Cytomegalovirus unique sequence long domain 84 (CMV-UL84) (Sarisky et al., J. Virol. 70(11): 7393–7413 (1996); and Schmolke et al., J. Virol. 71(9): 7048–7060 (1997)), Varicella-Zoster virus ORF 61 (VZV-ORF61) (Moriuchi et al. (1995), supra), Pseudorabies virus early protein 0 (PRV-EP0) (Moriuchi et al. (1995), supra), Human Cytomegalovirus immediate early protein (CMV-IE) 1 (Ahn et al, Mol. Cell. Biol. 18(8): 4899–4913 (1998)), CMV-IE2, CMV-IE86 (Bresnahan et al, J. Biol. Chem.

272(34): 22075–22082 (1998)), HIV-tat (Schafer et al., J. Virol. 70(10): 6937–6946 (1996)), HTLV-tax, HBV-X, AAV-Rep 78 (Weger et al., J. Virol. 71(11): 8437–8447 (1997)); Pereira et al., J. Virol. 71(2): 1079–1088 (1997); and Pasquale et al., J. Virol. 72(10): 7916–7925 (1998)), the cellular factor from the U2OS osteosarcoma cell line (U2OS) that functions like HSV ICP0 (Yao et al., J. Virol. 69(10): 6249–6258 (1995)), and the cellular factor in PC12 cells that is induced by nerve growth factor (Jordan et., J. Virol. 72(7): 5373–5382 (1998)). The HSV ICP0-like factor from the U2OS osteosarcoma cell line and the cellular factor in PC12 cells that is induced by nerve growth factor can be isolated, for example, by making cDNA from the cell line, cloning the cDNA into an adenoviral cosmid, constructing an adenoviral vector library that expresses the cDNA, and screening for the factor, such as by complementing for growth of an ICP0-deleted herpes vector and/or maintaining expression of CMV-driven GFP from the ICP0-deleted herpes vector, pulling out the complemented cells, and recovering the adenovirus vector containing and expressing the factor. Whether or not a given trans-acting factor can modulate a given transgene, including a transgene that is part of an expression cassette, can be determined in accordance with methods set forth in the Examples and other methods known in the art. A preferred trans-acting factor that is not from an adenovirus is HSV ICP0. Preferably, the transgene comprises a promoter from a cytomegalovirus or a Rous sarcoma virus or the transgene is part of an expression cassette that comprises such a promoter. The gene encoding the trans-acting factor preferably comprises an adenoviral E4 promoter. Preferably, the at least E4Δ adenoviral vector further comprises a cis-acting factor. The cis-acting factor can be of viral or cellular origin and can be under the control of a regulatable promoter, such as an inducible promoter or a repressible promoter, examples of which are recited above. Examples of cis-acting factors include a matrix attachment region (MAR) (e.g., immunoglobulin heavy chain μ (murine; Jenuwein et al., Nature 385(16): 269 (1997)), apolipoprotein B (human; Kalos et al., Molec. Cell. Biol. 15(1): 198–207 (1995)), papillomavirus type 16 (human; Tan et al., J. Virol. 72(5): 3610–3622 (1998)), and clotting factor VIII (human; Fallaux et al., Molec. Cell. Biol. 16(8): 4264–4272 (1996)), a locus control region (LCR), and a scaffold attachment region (SAR) (e.g., β-interferon (human; Agarwal et al., J. Virol 42(5): 3720–3728 (1998))). In the two vector embodiment, the viral vector preferably is an adenoviral vector or a *Herpes simplex* vector. The viral vector can further comprise a transgene, in which case the viral vector can further comprise a cis-acting factor.

In view of the above, the present invention further provides a recombinant at least E4Δ adenoviral vector for use in the single vector embodiment of the method. The vector comprises (i) a transgene and (ii) a gene encoding a trans-acting factor. The trans-acting factor modulates the persistence of expression of the transgene. The gene encoding the trans-acting factor is not from the E4 region of an adenovirus. A preferred trans-acting factor that is not from the E4 region of an adenovirus is pTP. Preferably, the gene encoding the trans-acting factor is not from an adenovirus. Examples of trans-acting factors that are not from an adenovirus include HSV ICP0, CMV UL84, VZV-ORF61, PRV-EP0, CMV-IE1, CMV-IE2, CMV-IE86, HIV-tat, HTLV-tax, HBV-X, AAV-Rep 78, the cellular factor from the U2OS osteosarcoma cell line that functions like HSV ICP0, and the cellular factor in PC12 cells that is induced by nerve growth factor. A preferred trans-acting factor that is not from an adenovirus is HSV ICP0. The transgene preferably comprises a promoter from a cytomegalovirus or a Rous sarcoma virus or the transgene is part of an expression cassette that comprises such a promoter. The gene encoding the trans-acting factor preferably comprises an adenoviral E4 promoter. Preferably, the vector further comprises a cis-acting factor. Examples of cis-acting factors include an MAR (e.g., immunoglobulin heavy chain μ (murine), apolipoprotein B (human), papillomavirus type 16 (human) and clotting factor VIII (human)), an LCR or an SAR (e.g., β-interferon (human)).

Also in view of the above, the present invention further provides a system for modulation of a transgene in an at least E4Δ adenoviral vector. The system comprises (i) an at least E4Δ adenoviral vector comprising a transgene and (ii) a gene encoding a trans-acting factor. The trans-acting factor modulates the persistence of expression of the transgene. The gene encoding the trans-acting factor is not the E4 region of an adenovirus. The at least E4Δ adenoviral vector comprises the gene encoding the trans-acting factor or the system further comprises a viral vector, in which case the viral vector comprises the gene encoding the trans-acting factor. A preferred trans-acting factor that is not from the E4 region of the adenovirus is pTP. Preferably, the gene encoding the trans-acting factor is not from an adenovirus. Examples of trans-acting factors that are not from an adenovirus include HSV ICP0, CMV UL84, VZV-ORF61, PRV-EP0, CMV-IE1, CMV-IE2, CMV-IE86, HIV-tat, HTLV-tax, HBV-X, AAV-Rep 78, the cellular factor from the U2OS osteosarcoma cell line that functions like HSV ICP0, and the cellular factor in PC12 cells that is induced by nerve growth factor. A preferred trans-acting factor that is not from an adenovirus is HSV ICP0. The transgene preferably comprises a promoter from a cytomegalovirus or a Rous sarcoma virus or the transgene is part of an expression cassette that comprises such a promoter. The gene encoding the trans-acting factor preferably comprises an adenoviral E4 promoter. Preferably, the viral vector is an adenoviral vector or a *Herpes simplex* vector. The viral vector can further comprise a transgene and/or a cis-acting factor. Preferably, the at least E4Δ adenoviral vector further comprises a cis-acting factor. Examples of cis-acting factors include an MAR (e.g., immunoglobulin heavy chain μ (murine), apolipoprotein B (human), papillomavirus type 16 (human) and clotting factor VIII (human)), an LCR or an SAR (e.g., β-interferon (human)).

In the context of the present invention, the adenoviral vector can be derived from any adenovirus. An "adenovirus" is any virus of the family Adenoviridae, and desirably is of the genus Mastadenovirus (e.g., mammalian adenoviruses) or Aviadenovirus (e.g., avian adenoviruses). The adenovirus can be of any serotype. Adenoviral stocks that can be employed as a source of adenovirus can be amplified from the adenoviral serotypes 1 through 47, which are currently available from the American Type Culture Collection (ATCC, Rockville, Md.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, however, an adenovirus is of serotype 2, 5 or 9. Desirably, an adenovirus comprises coat proteins (e.g., penton base, hexon, and/or fiber) of the same serotype. However, also preferably, one or more coat proteins can be chimeric, in the sense, for example, that all or a part of a given coat protein can be from another serotype.

Although the vector preferably is an adenoviral vector or a *Herpes simplex* viral vector, it can be any other suitable vector, preferably a viral vector. For example, the viral vector can be an adeno-associated viral vector. In embodiments of the invention where the methods and compositions are drawn to non-Herpes vectors comprising HSV ICP0, the vector is preferably an adenoviral vector.

Although the vector (e.g., the non-Herpes vector, and the at least E4Δ adenoviral vector), in the context of the present invention, can be replication-competent, preferably, these vectors are replication-deficient or conditionally replication-deficient. Alternatively and preferably, the viral vector (and/or vector), which is preferably an adenoviral vector or a *Herpes simplex* viral vector, comprises a genome with at least one modification therein, optimally a modification that renders the virus replication-deficient. The modification to the viral genome includes, but is not limited to, deletion of a DNA segment, addition of a DNA segment, rearrangement of a DNA segment, replacement of a DNA segment, or introduction of a DNA lesion. A DNA segment can be as small as one nucleotide or as large as 36 kilobase pairs, i.e., the approximate size of the adenoviral genome, or 38 kilobase pairs, which is the maximum amount that can be packaged into an adenoviral virion. Preferred modifications, in addition to a modification that renders the vector replication-deficient, include insertion of (i) a transgene, (ii) a gene encoding a trans-acting factor and (iii) a cis-acting factor, as described above.

A virus, such as an adenovirus, also preferably can be a cointegrate, i.e., a ligation of viral, such as adenoviral, genomic sequences with other sequences, such as those of a plasmid, phage or other virus. In terms of an adenoviral vector (particularly a replication-deficient adenoviral vector), such a vector can comprise either complete capsids (i.e., including a viral genome, such as an adenoviral genome) or empty capsids (i.e., in which a viral genome is lacking, or is degraded, e.g., by physical or chemical means).

To the extent that it is preferable or desirable to target a virus, such as an adenovirus, to a particular cell, the virus can be employed essentially as an endosomolytic agent in the transfer into a cell of plasmid DNA, which contains a marker gene and is complexed and condensed with polylysine covalently linked to a cell-binding ligand, such as transferrin (Cotten et al., PNAS (USA) 89: 6094–6098 (1992); and Curiel et al., PNAS (USA) 88: 8850–8854 (1991)). It has been demonstrated that coupling of the transferrin-polylysine/DNA complex and adenovirus (e.g., by means of an adenovirus-directed antibody, with transglutaminase, or via a biotin/streptavidin bridge) substantially enhances gene transfer (Wagner et al., PNAS (USA) 89: 6099–6103 (1992)).

Alternatively, one or more viral coat proteins, such as the adenoviral fiber, can be modified, for example, either by incorporation of sequences for a ligand to a cell-surface receptor or sequences that allow binding to a bi-specific antibody (i.e., a molecule with one end having specificity for the fiber, and the other end having specificity for a cell-surface receptor) (PCT international patent application no. WO 95/26412 (the '412 application) and Watkins et al., "Targeting Adenovirus-Mediated Gene Delivery with Recombinant Antibodies," Abst. No. 336). In both cases, the typical fiber/cell-surface receptor interactions are abrogated, and the virus, such as an adenovirus, is redirected to a new cell-surface receptor by means of its fiber.

Alternatively, a targeting element, which is capable of binding specifically to a selected cell type, can be coupled to a first molecule of a high affinity binding pair and administered to a host cell (PCT international patent application no. WO 95/31566). Then, a gene delivery vehicle coupled to a second molecule of the high affinity binding pair can be administered to the host cell, wherein the second molecule is capable of specifically binding to the first molecule, such that the gene delivery vehicle is targeted to the selected cell type.

Along the same lines, since methods (e.g., electroporation, transformation, conjugation of triparental mating, (co-)transfection, (co-)infection, membrane fusion, use of microprojectiles, incubation with calcium phospate-DNA precipitate, direct microinjection; etc.) are available for transferring viruses, plasmids, and phages in the form of their nucleic acid sequences (i.e., RNA or DNA), a vector similarly can comprise RNA or DNA, in the absence of any associated protein, such as capsid protein, and in the absence of any envelope lipid. Similarly, since liposomes effect cell entry by fusing with cell membranes, a vector can comprise liposomes, with constitutive nucleic acids encoding the coat protein. Such liposomes are commercially available, for instance, from Life Technologies, Bethesda, Md., and can be used according to the recommendation of the manufacturer. Moreover, a liposome can be used to effect gene delivery and liposomes having increased transfer capacity and/or reduced toxicity in vivo can be used. The soluble chimeric coat protein (as produced using methods described herein) can be added to the liposomes either after the liposomes are prepared according to the manufacturer's instructions, or during the preparation of the liposomes.

In terms of the production of vectors according to the invention (including recombinant adenoviral vectors, recombinant viral vectors and transfer vectors), standard molecular and genetic techniques, such as those known to those skilled in the art, are used. Vectors comprising virions or viral particles (e.g., recombinant adenoviral vectors) can be produced using viral vectors in the appropriate cell lines. Similarly, particles comprising one or more chimeric coat proteins can be produced in standard cell lines, e.g., those currently used for adenoviral vectors. These resultant particles then can be targeted to specific cells.

Alterations of the native amino acid sequence to produce variant peptides can be done by a variety of means known to those skilled in the art. A variant peptide is a peptide that is substantially homologous to a given peptide, but which has an amino acid sequence that differs from that peptide. The degree of homology (i.e., percent identity) can be determined, for instance, by comparing sequence information using a computer program optimized for such comparison (e.g., using the GAP computer program, version 6.0 or a higher version, described by Devereux et al. (Nucleic Acids Res. 12: 387 (1984)), and freely available from the University of Wisconsin Genetics Computer Group (UWGCG)). The activity of the variant proteins and/or peptides can be assessed using other methods known to those skilled in the art.

In terms of amino acid residues that are not identical between the variant protein (peptide) and the reference protein (peptide), the variant proteins (peptides) preferably comprise conservative amino acid substitutions, i.e., such that a given amino acid is substituted by another amino acid of similar size, charge density, hydrophobicity/hydrophilicity, and/or configuration (e.g., Val for Phe). The variant site-specific mutations can be introduced by ligating into an expression vector a synthesized oligonucleotide comprising the modified site. Alternately, oligonucleotide-directed site-specific mutagenesis procedures can be used, such as those disclosed in Walder et al., Gene 42: 133 (1986); Bauer et al., Gene 37: 73 (1985); Craik, Biotechniques, January 1995: 12–19; and U.S. Pat. Nos. 4,518,584 and 4,737,462.

Any appropriate expression vector (e.g., as described in Pouwels et al., *Cloning Vectors: A Laboratory Manual* (Elsevier, N.Y.: 1985)) and corresponding suitable host cell can be employed for production of a recombinant peptide or protein in a host cell. Expression hosts include, but are not limited to, bacterial species within the genera Escherichia, Bacillus, Pseudomonas, Salmonella, mammalian or insect host cell systems, including baculoviral systems (e.g., as described by Luckow et al., Bio/Technology 6: 47 (1988)), and established cell lines, such as COS-7, C127, 3T3, CHO, HeLa, BHK, and the like. An especially preferred expression system for preparing chimeric proteins (peptides) according to the invention is the baculoviral expression system wherein *Trichoplusia ni*, Tn 5B1-4 insect cells, or other appropriate insect cells, are used to produce high levels of recombinant proteins. The ordinary skilled artisan is, of course, aware that the choice of expression host has ramifications for the type of peptide produced. For instance, the glycosylation of peptides produced in yeast or mammalian cells (e.g., COS-7 cells) will differ from that of peptides produced in bacterial cells, such as *Escherichia coli*.

Covalently-bound complexes can be prepared by linking a chemical moiety to a functional group on the side chain of an amino acid of a peptide or protein or at the N- or C-terminus of the peptide or protein. Such modifications can be particularly useful, for instance, in constructing a bi-specific or a multi-specific molecule comprising a ligand to a cell-surface receptor attached to an antibody. Further modifications will be apparent to those of ordinary skill in the art.

Viral attachment, entry and gene expression can be evaluated initially by using the adenoviral vector containing the insert of interest to generate a recombinant virus expressing the desired protein or RNA and a marker gene, such as β-galactosidase. β-galactosidase expression in cells infected with adenovirus containing the β-galactosidase gene (Ad-LacZ) can be detected as early as two hours after adding Ad-LacZ to cells. This procedure provides a quick and efficient analysis of cell entry of the recombinant virus and gene expression, and is implemented readily by an artisan of ordinary skill using conventional techniques.

The methods, vectors, modulation systems and compositions of the present invention have utility in vitro, such as in the study of viral clearance and modulation of persistence of transgene expression. Similarly, the present inventive methods, vectors, modulation systems and compositions have utility in vivo. For example, a present inventive vector can be used to treat any one of a number of diseases by delivering to cells corrective DNA, e.g., DNA encoding a function that is either absent or impaired. Diseases that are candidates for such treatment include, for example, cancer, e.g., melanoma or glioma, cystic fibrosis, genetic disorders, and pathogenic infections, including HIV infection. Other applications of the methods and constituents of the present invention will be apparent to those skilled in the art.

One skilled in the art will appreciate that many suitable methods of administering a vector (i.e., an adenoviral vector or a viral vector), system for modulation or composition of either of the foregoing to an animal for purposes of gene expression, such as in the context of gene therapy (see, for example, Rosenfeld et al., Science 252: 431–434 (1991); Jaffe et al., Clin. Res., 39(2): 302A (1991); Rosenfeld et al., Clin. Res. 39(2): 311A (1991); Berkner, BioTechniques 6: 616–629 (1988)) are available, and, although more than one route can be used for administration, a particular route can provide a more immediate and more effective reaction than another route. Pharmaceutically acceptable excipients for use in administering a vector also are well-known to those who are skilled in the art, and are readily available. The choice of excipient will be determined in part by the particular method used to administer the vector. Accordingly, the present invention provides a composition comprising the recombinant at least E4Δ adenoviral vector and a carrier therefor and a composition comprising the system for modulation of the recombinant at least E4Δ adenoviral vector and a carrier therefor. In this regard, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, emulsions, gels, and the like containing, in addition to the active ingredient, such excipients as are known in the art.

Aerosol formulations can be made for administration via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, suppositories can be made with the use of a variety of bases, such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the transgene of interest, the composition employed, the method of administration, and the particular site and organism being treated. However, preferably, a dose corresponding to an effective amount of a vector (e.g., an adenoviral vector according to the invention) is employed. An "effective amount" is one that is sufficient to achieve transgene expression in a cell or to produce a desired effect, e.g., a prophylactic or therapeutic effect, in a host, which can be monitored using several end-points known to those skilled in the art. For instance, one desired effect is nucleic acid transfer to a host cell. Such transfer can be monitored by a variety of means, including, but not limited to, evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer) or a therapeutic effect (e.g., alleviation of some symptom associated with the disease, condition, disorder or syndrome being treated). These methods described are by no means all-inclusive, and further methods to suit the specific application will be apparent to the ordinary skilled artisan. In this regard, it should be noted that the response of a host to the introduction of a vector can vary depending on the dose of the vector administered, the site of delivery, and the genetic makeup of the vector as well as the transgene, itself.

Generally, to ensure effective transfer of the vectors of the present invention, it is preferred that about 1 to about 5,000 copies of the vector according to the invention be employed per cell to be contacted, based on an approximate number of cells to be contacted in view of the given route of administration, and it is even more preferred that about 3 to about 300 pfu enter each cell. However, this is merely a general guideline, which by no means precludes use of a higher or lower amount, as might be warranted in a particular application, either in vitro or in vivo. The actual dose and schedule can vary depending on whether the composition is administered in combination with other compositions, e.g., pharmaceutical compositions, or depending on interindividual differences in pharmacokinetics, drug disposition, and metabolism. Similarly, amounts can vary in in vitro applications depending on the particular type of cell or the means by which the vector is transferred. One skilled in the art easily can make any necessary adjustments in accordance with the necessities of the particular situation.

EXAMPLES

The following examples serve to illustrate the present invention and are not intended to limit its scope in any way.

Example 1

This example demonstrates the level of transgene expression obtained in cell culture with an at least E4Δ adenoviral vector comprising secretory alkaline phosphatase as the transgene and HSV ICP0 or Ad pTP as the trans-acting factor.

A DNA fragment comprising the coding region of the gene encoding the trans-acting factor HSV ICP0 or Ad pTP was operably linked to the adenoviral E4 promoter (Ad E4 pro) and an SV40 poly A region in an E4Δ adenoviral vector using methods of vector construction known to those of ordinary skill in the art. In addition, the E4Δ adenoviral vector was modified to comprise a DNA fragment comprising the coding region of the human secretory alkaline phosphatase (SAP) gene operably linked to the cytomegalovirus immediate early promoter (CMVie pro) and an SV40 poly A region using well-known methods of vector construction.

Primary human embryonic lung fibroblasts (HEL) cells were infected with one of the following vectors: (i) a mock vector, (ii) an E1ΔE4Δ adenoviral vector, (iii) an E1ΔE4Δ adenoviral vector comprising the SAP coding region operably linked to the CMVie pro and an SV40 poly A region, (iv) an E1ΔE4Δ adenoviral vector comprising the SAP coding region operably linked to the CMVie pro and an SV40 poly A region and the coding region of HSV ICP0 operably linked to Ad E4 pro and an SV40 poly A region, and (v) an E1ΔE4Δ adenoviral vector comprising the SAP coding region operably linked to the CMVie pro and an SV40 poly A region and the coding region of Ad pTP operably linked to Ad E4 pro and an SV40 poly A region. SAP expression (RLU/2 $\mu$l medium) was measured as a function of multiplicity of infection (moi; particles/cell) to generate a dose-response curve. SAP expression ranged from about 1,000 to about $1 \times 10^7$ RLU/2 $\mu$l medium for an moi ranging from about 1 to about 1,000 particles/cell compared to control (i.e., a mock vector).

Example 2

This example demonstrates that HSV ICP0 can modulate a transgene in an E4Δ adenoviral vector and, thereby, modulate persistence of transgene expression in cell culture.

HEL cells were also infected with one of the following vectors: (i) a mock vector, (ii) approximately 100 particles/cell of an E1Δ adenoviral vector comprising the SAP coding region operably linked to the CMVie pro and an SV40 poly A region, (iii) approximately 1,000 particles/cell of (ii), (iv) approximately 100 particles/cell of an E1ΔE4Δ adenoviral vector comprising the SAP coding region operably linked to the CMVie pro and an SV40 poly A region, (v) approximately 1,000 particles/cell of (iv), (vi) approximately 100 particles/cell of an E1ΔE4Δ adenoviral vector comprising the SAP coding region operably linked to the CMVie pro and an SV40 poly A region and the coding region of HSV ICP0 operably linked to AdE4 pro and an SV40 poly A region, and (vii) approximately 1,000 particles/cell of (vi) in order to measure SAP expression (RLU/2 $\mu$l medium) as a function of days post-infection. While expression with SAP was relatively high in HEL cells infected with 1,000 particles/cell of either of the E1Δ adenoviral vector or the E1Δ4Δ adenoviral vector, no expression was detected after around 15 days post-infection. In contract, SAP expression was maintained at a relatively high level in HEL cells infected with 1,000 particles/cell of the ICP0-expressing E1ΔE4Δ adenoviral vector as long as 28 days post-infection. SAP expression was also detected at 28 days post-infection in HEL cells infected with 100 particles/cell of either of the ICP0-expressing E1ΔE4Δ adenoviral vector or the E1Δ adenoviral vector, although at comparatively lower levels. Substantially lower levels of SAP expression was detected in HEL cells infected with 100 particles/cell of E1ΔE4Δ adenoviral vector up to about 24 days post-infection. These results demonstrate that HSV ICP0 can modulate a transgene in an E4Δ adenoviral vector and, thereby, modulate persistence of transgene expression. Similar results were also obtained in a human retinal pigmented epithelial cells (HRPE-19) at approximately 33 days post-infection.

Example 3

This example demonstrates that Ad pTP can modulate a transgene in an E4Δ adenoviral vector and, thereby, modulate persistence of transgene expression in cell culture.

SAP expression (RLU/2 µl medium) as a function of days post-infection was also measured for HEL cells infected with one of the following vectors: (i) a mock vector, (ii) approximately 100 particles/cell of an E1Δ adenoviral vector comprising the SAP coding region operably linked to CMVie pro and an SV40 poly A region, (iii) approximately 100 particles/cell of an E1ΔE4Δ adenoviral vector comprising the SAP coding region operably linked to CMVie pro and an SV40 poly A region, (iv) approximately 100 particles/cell of an E1ΔE4Δ adenoviral vector comprising the SAP coding region operably linked to CMVie pro and an SV40 poly A region and the coding region of Ad pTP operably linked to AdE4 pro and an SV40 poly A region, and (v) approximately 1,000 particles/cell of (iv). While SAP expression was detected at about 28 days post-infection for all test vectors except (iii), for which expression was not detected past about 24 days post-infection, SAP expression was highest at 28 days post-infection in cells infected with 1,000 particles/cell of Ad pTP-expressing E1ΔE4Δ adenoviral vector. These results demonstrate that Ad pTP can modulate a transgene in an E4Δ adenoviral vector and, thereby, modulate persistence of transgene expression. Similar results were also obtained in HRPE-19 cells at approximately 30 days post-infection.

Example 4

This example demonstrates that HSV ICP0 and Ad pTP can modulate a transgene in an intravenously administered E4Δ adenoviral vector and, thereby, modulate persistence of transgene expression in vivo.

Nude mice were intravenously injected with one of the following vectors: (i) approximately $1\times10^{10}$ particles of an E1Δ adenoviral vector comprising the SAP coding region operably linked to the CMVie pro and an SV40 poly A region, (ii) approximately $1\times10^{10}$ particles of an E1ΔE4Δ adenoviral vector comprising the SAP coding region operably linked to the CMVie pro and an SV40 poly A region, (iii) approximately $1\times10^{10}$ particles of an E1ΔE4Δ adenoviral vector comprising the SAP coding region operably linked to the CMVie pro and an SV40 poly A region and the HSV ICP0 coding region operably linked to the E4 promoter and an SV40 poly A region, (iv) approximately $5\times10^{10}$ particles of (iii), and (v) approximately $1\times10^{10}$ particles of an E1ΔE4Δ adenoviral vector comprising the SAP coding region operably linked to the CMVie pro and an SV40 poly A region and the Ad pTP coding region operably linked to the E4 promoter and an SV40 poly A region. At approximately 22 days post-infection, high levels of SAP expression was maintained with HSV ICP0-expressing and Ad pTP-expressing E4Δ adenoviral vectors.

Example 5

This example demonstrates that HSV ICP0 and Ad pTP can modulate a transgene in an intramuscularly administered E4Δ adenoviral vector and, thereby, modulate persistence of transgene expression in vivo.

Nude mice were intramuscularly injected with one of the following vectors: (i) approximately $1\times10^{10}$ particles of an E1Δ adenoviral vector comprising the SAP coding region operably linked to the CMVie pro and an SV40 poly A region, (ii) approximately $5\times10^{10}$ particles of (ii), (iii) approximately $1\times10^{10}$ particles of an E1ΔE4Δ adenoviral vector comprising the SAP coding region operably linked to the CMVie pro and an SV40 poly A region, (iv) approximately $5\times10^{10}$ particles of (iii), (v) approximately $1\times10^{10}$ particles of an E1ΔE4Δ adenoviral vector comprising the SAP coding region operably linked to the CMVie pro and an SV40 poly A region and the HSV ICP0 coding region operably linked to the E4 promoter and an SV40 poly A region, (vi) approximately $5\times10^{10}$ particles of (v), and (vii) approximately $1\times10^{10}$ particles of an E1ΔE4Δ adenoviral vector comprising the SAP coding region operably linked to the CMVie pro and an SV40 poly A region and the Ad pTP coding region operably linked to the E4 promoter and an SV40 poly A region. At approximately 18 days post-infection, high levels of SAP expression was maintained with HSV ICP0-expressing and Ad pTP-expressing E4Δ adenoviral vectors.

Example 6

This example demonstrates the ability of a non-Herpes vector comprising a gene encoding HSV ICP0 to modulate the expression of a transgene in a cell in a host by reducing the number of neutralizing antibodies produced by the host against the vector.

C57BL/6 mice were given intratracheal administration of either (i) approximately $5\times10^{10}$ particles of an E1Δ adenoviral vector comprising the SAP coding region operably linked to the CMVie pro and an SV40 poly A region and (ii) approximately $5\times10^{10}$ particles of an E1ΔE4Δ adenoviral vector comprising the SAP coding region operably linked to the CMVie pro and an SV40 poly A region, and (iii) approximately $5\times10^{10}$ particles of an E1ΔE4Δ adenoviral vector comprising the SAP coding region operably linked to the CMVie pro and an SV40 poly A region and the HSV ICP0 coding region operably linked to the E4 promoter and an SV40 poly A region. Neutralizing antibody titer in the serum was measured at 14 days and 21 days after administration. The approximate averages for each antibody titer measured at both time points are set forth in Table 1.

TABLE 1

Effect of HSV ICP0 on Neutralizing Antibodies Against Adenoviral Vectors (Reciprocal Dilution)

| Days post administration | E1Δ – HSV ICP0(–) | E1E4Δ – HSV ICP0(–) | E1E4Δ – HSV ICP0(+) |
|---|---|---|---|
| 14 days | 45 | 75 | 15 |
| 21 days | 95 | 40 | 30 |

As can be seen in Table 1, adenoviral vectors comprising a gene encoding HSV ICP0 resulted in a lower production of neutralizing antibodies produced against the adenoviral vector by the host than in comparison to similar vectors not containing a gene for HSV ICP0. These results indicate that non-Herpes vectors, such as adenoviral vectors, comprising a gene encoding HSV ICP0 result in a lower immune response against the HSV ICP0-expressing vector and thus result in modulation of transgene expression.

All references, including publications, patent applications and patents, cited herein are hereby incorporated by reference to the same extent as if each reference were individually and specifically indicated to be incorporated by reference and were set forth in its entirety herein. The use of the terms "a" and "an" and "the" and similar referents (e.g., "the vector" or "an adenoviral vector") in the context of describing the present invention (especially in the context of the following claims) should be construed to cover both the singular and the plural, unless otherwise indicated herein or clearly contradicted by context.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of modulating the persistence of expression of a transgene in a cell, wherein the transgene is operably linked to a Rous sarcoma viral promoter or a cytomegaloviral promoter or the transgene is part of an expression cassette that comprises such a promoter, which method comprises contacting the cell with a non-Herpes viral vector comprising and expressing a gene encoding HSV ICP0, whereupon expression of HSV ICP0, the persistence of expression of the transgene is modulated as compared to the persistence of expression of the transgene in the absence of expression of HSV ICP0.

2. The method of claim 1, wherein the non-Herpes viral vector further comprises a cis-acting element.

3. The method of claim 1, wherein the transgene is present on a viral vector, in which case the method further comprises contacting the cell with the viral vector.

4. The method of claim 3, wherein the non-Herpes viral vector and/or the viral vector further comprises a cis-acting element.

5. A system for modulating the persistence of expression of a transgene, which system comprises:

(i) a non-Herpes viral vector comprising a gene encoding HSV ICP0 and (ii) a transgene, wherein the transgene is operably linked to a Rous sarcoma viral promoter or a cytomegaloviral promoter, optionally as part of an expression cassette, wherein the HSV ICP0 modulates the persistence of expression of the transgene and either the non-Herpes viral vector comprises the transgene or the transgene is present on a viral vector, in which case the system further comprises the viral vector.

6. (Currently Amended) The system of claim 5, wherein the non-Herpes viral vector and/or the viral vector further comprises a cis-acting element.

* * * * *